United States Patent [19]

Coker et al.

[11] Patent Number: 4,757,074
[45] Date of Patent: Jul. 12, 1988

[54] PIPERAZINYL BENZYL ACIDS HAVING ANTIHISTAMINE ACTIVITY

[75] Inventors: Geoffrey G. Coker, Bromley, England; John W. A. Findlay, Chapel Hill, N.C.

[73] Assignee: Burroughs Wellcome Co., Research Triangle Park, N.C.

[21] Appl. No.: 833,665

[22] Filed: Feb. 24, 1986

Related U.S. Application Data

[62] Division of Ser. No. 635,250, Jul. 27, 1984, abandoned.

[30] Foreign Application Priority Data

Aug. 1, 1983 [GB] United Kingdom ............... 8320701

[51] Int. Cl.$^4$ .................. A61K 31/495; C07D 295/00
[52] U.S. Cl. ..................................... 514/255; 544/396; 544/397
[58] Field of Search ................. 544/396, 397; 514/255

[56] References Cited

U.S. PATENT DOCUMENTS

| | | | |
|---|---|---|---|
| 2,630,435 | 3/1953 | Baltzly et al. | 544/396 |
| 2,636,032 | 4/1953 | Weston et al. | 544/396 |
| 2,709,169 | 5/1955 | Morren | 544/396 |
| 2,861,072 | 11/1958 | Weston et al. | 544/396 |
| 3,868,377 | 2/1975 | Raabe et al. | 544/396 |
| 4,146,582 | 3/1979 | Maggioni | 568/425 |
| 4,397,855 | 8/1983 | Sircar | 544/396 |

FOREIGN PATENT DOCUMENTS

| | | |
|---|---|---|
| 177779 | 3/1954 | Belgium . |
| 58146 | 8/1982 | European Pat. Off. . |
| 980251 | 1/1965 | United Kingdom . |
| 1528862 | 10/1978 | United Kingdom . |

OTHER PUBLICATIONS

Sircar, Chem. Abst., 100:6551k, (1984).
Meuldermans et al., Chem. Abst. 99:133255c.
Baltes et al., Chem. Abst, 98:34599r.

*Primary Examiner*—Donald G. Daus
*Assistant Examiner*—Cecilia Shen
*Attorney, Agent, or Firm*—Donald Brown

[57] ABSTRACT

The present invention provides compounds of the formula (I):

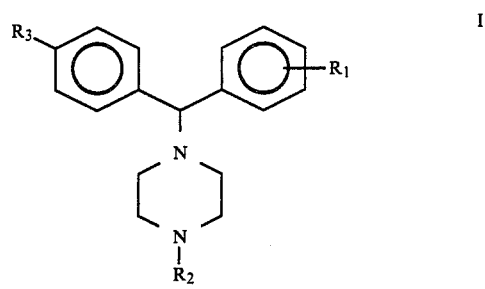

or salts, esters or amide derivatives thereof, wherein $R_1$ is $-CO_2H$, $-CH=CH-CO_2H$, $-(CH_2)_nCO_2H$, or $-O-(CH_2)_nCO_2H$ (n=1 to 4); $R_2$ is $C_{1\alpha}$ alkyl or benzyl which is optionally substituted by a $C_{1-4}$ alkyl group or groups; $R_3$ is $C_{1-4}$ alkoxy, $C_{1-4}$ alkyl or halogen. Also provided are pharmaceutical formulations containing the compounds of the formula (I) and methods for the preparation of the compounds. The above mentioned compounds have antihistaminic activity.

3 Claims, No Drawings

PIPERAZINYL BENZYL ACIDS HAVING ANTIHISTAMINE ACTIVITY

This application is a division of application Ser. No. 635,250, filed 7/27/84, now abandoned.

The present invention relates to new chemical compounds exhibiting antihistamine activity with low sedative potential.

U.S. Pat. No. 2,630,435 discloses a group of N-benzhydrylpipera zines with antihistamine activity, the most outstanding of which is the compound named 1-(4-Chlorobenzhydryl)-4-methylpiperazine and hereinafter referred to by its generic name, chlorcyclizine. Chlorcyclizine has gained a fair degree of clinical acceptance. However, like all other potent antihistamines in clinical use it produces sedation and drowsiness in varying degrees in most patients (L. Goodman and A. Gilman, *The Pharmacological Basis of Therapeutics*, 4th ed., p. 640, Macmillan, N.Y., 1970). This sedating effect limits the use of antihistamines by patients who must operate machinery, drive motor vehicles or must engage in activities requiring mental alertness.

A novel group of compounds having potent antihistamine activity which are substantially free from sedative effects, and which will have little or no anticholinergic effect has now been discovered.

Accordingly this invention provides the compounds of formula I.

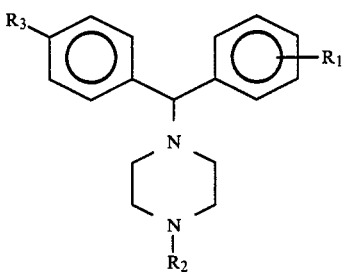

I wherein $R_1$ is —COOH, —CH=CH—COOH, —(CH$_2$)$_n$COOH, or —O—(CH$_2$)$_n$ COOH (n=1 to 4). $R_2$ is alkyl (1-4 carbons) or benzyl which may bear alkyl substituents of 1-4 carbons. $R_3$ is alkoxy (1-4 carbons), alkyl (1-4 carbons), or halogen.

This invention also includes ester and amide derivatives as well as acid addition salts and salts of the carboxylic acid group the compounds of formula (I).

The compounds of formula (I) which were found to be particularly active are:

| Compound | Example No. | $R_1$ | $R_2$ | $R_3$ |
|---|---|---|---|---|
| A | 1 | 3,-CH=CH—CO$_2$H | —CH$_3$ | —Cl |
| B | 2 | 3,-COOH | —CH$_3$ | —Cl |
| C | 3 | 2,-COOH | —CH$_3$ | —Cl |
| D | 4 | 4,-COOH | —CH$_3$ | —Cl |
| E | 5 | 3-COOH | —CH$_3$ | —OCH$_3$ |
| F | 6 | 3-OCH$_2$COOH | —CH$_3$ | Cl |
| G | 7 | 3-OCH$_2$COOH | —CH$_2$-C$_6$H$_4$-CH$_3$ | Cl |
| H | 8 | 3-OCH$_2$COOH | —CH$_2$-C$_6$H$_4$-C(CH$_3$)$_3$ | Cl |

Compounds of formula (I) and their salts may be synthesized by methods known in the art for the synthesis of compounds having analogous structures.

1. A method for preparing compounds of formula (I) when $R_1$ is —C≡C—COOH (trans) comprises reacting a compound (II) in the presence of palladium with a protected form of acrylic acid such as an ester followed by deprotection of the acid group, e.g. hydrolysis.

Alternatively, compounds of formula (II) may be treated with n-butyllithium followed by dimethylformamide to give the corresponding benzaldehyde of formula IIa

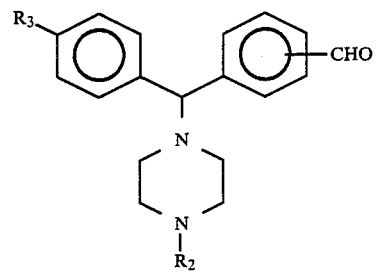

wherein $R_2$ and $R_3$ are as herein before defined, which is then converted to compounds of formula (I) by the well-known Knoevenagel reaction with malonic acid or by Wittig reaction with an appropriate reagent such as (C$_2$H$_5$O)$_2$POCH$_2$CO$_2$C$_2$H$_5$, followed by basic hydrolysis.

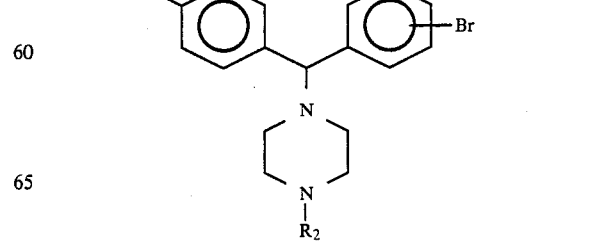

II

Compounds of formula (II) may be prepared by reacting a compound of formula (III) wherein L is a leaving group as defined by J. March, *Advanced Organic Chemistry*, 2nd ed., pp. 683 and 895, McGraw-Hill, New York, 1977, e.g. —Br, —Cl, toluene sulphonate, etc. with a piperazine (IV).

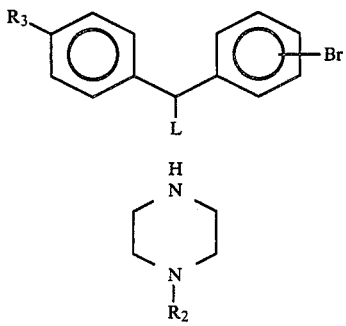

$R_2$ and $R_3$ are as defined above.

In turn compounds of formula (III) when L is Cl can be prepared by treatment of compounds of formula (V) with agents such as $SOCl_2$. Compounds of formula (V) can be obtained by reacting a compound of formula (VI) with n-butyllithium followed by condensation with the compound of formula (VII).

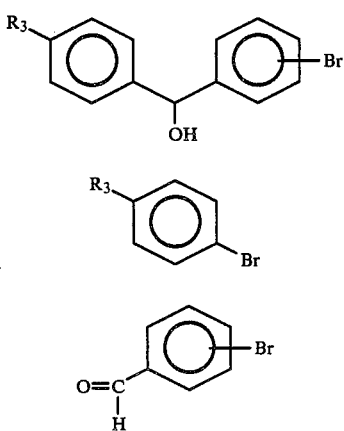

2. When the compounds of formula (I) have the carboxylic acid group directly on the phenyl ring preparation consists of reacting a compound of formula (II) with a suitable metallating reagent to produce a compound of formula (VIII) where M is an alkaline or alkaline earth metal.

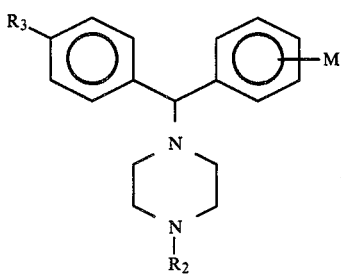

For example n-butyllithium or magnesium with an appropriate solvent can be used to produce the lithium or magnesium (Grignard reagent) respectively. Compounds of formula (VII) can be reacted with carbon dioxide to yield the corresponding compounds of formula (I).

3. Compounds of formula (I) when $R_1$ is —O($CH_2$)$_n$COOH can be prepared by deprotecting compounds of formula (IX), (wherein $R_4$ is methyl, benzyl, or other suitable protecting group) by known methods, e.g. with boron tribromide where $R_4$ is methyl or benzyl, followed by base-catalyzed reaction of the resulting phenol with compounds of formula (X), wherein L is defined as above and $R_5$ is lower alkyl or benzyl. The resulting ester may then be hydrolized to give the free acid.

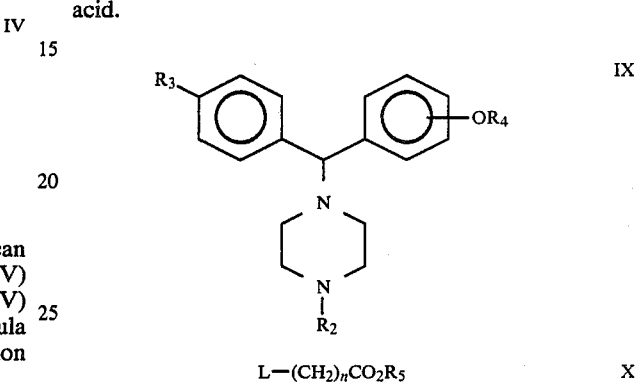

Compounds of formula (IX) can be prepared by methods analogous to those used in the preparation of compounds of formula (II), with Br replaced throughout by —$OR_4$.

4. Compounds of formula (I) where $R_1$ is —($CH_2$)$_n$COOH can be prepared from arylalkyl ketones of formula (XI) by application of the Willgerodt reaction (J. March, op. cit., p 1140) followed by hydrolysis of the resulting amide.

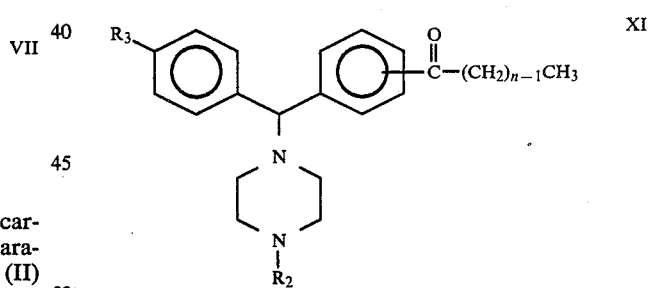

Compounds of formula (XI) can be obtained from compounds of formula (II) by treatment with n-butyllithium followed by $CH_3(CH_2)_{n-1}CON(CH_3)_2$.

Alternatively, compounds of formula (I) where $R_1$ is —($CH_2$)$_2$COOH may be prepared by reduction, e.g. with hydrogen and platinum, of compounds of formula (I) where $R_1$ is —CH=CHCOOH.

Compounds of this invention have the same utilities as antihistamines used clinically at present. They may be used to relieve symptoms of nasal stuffiness due to colds and vasomotor rhinitis and for the symptomatic control of all allergic conditions including nasal allergy, perennial rhinitis urticaria, angioneurotic oedema, allergic conjunctivitis, food allergy, drug and serum reactions, insect bites and stings and desensitizing reactions. The compounds are also indicated in all conditions responsive to its antipruritic activity including allergic dermatoses, neurodermatitis, anogenital pruritus, and pruritus of non-specific origin such as eczema, and of specific cause such as chickenpox, photosensitivity and sunburn. In contrast to the antihistamines in present use, the compounds of this invention are not sedating and have little or no anticholinergic side effects.

The amount of active compound required for use in the above conditions will vary both with the route of administration, the condition under treatment and the mammal undergoing treatment, and is ultimately at the discretion of the physician. A suitable oral dose of the active compound for a mammal is in the range of from 0.3 to 6.0 mg per kilogram body weight per day; preferably from 0.9 to 3.0 mg/kg. For example a typical dose for a human recipient of compound (A) is 2.1 mg/kg body weight per day.

The desired daily dose is preferably presented as from one to six sub-doses administered at appropriate intervals throughout the day as needed. Where three sub-doses of compounds of formula (I) are employed, each will preferably lie in the range of from 0.3 to 1.0 mg/kg body weight; for example, a typical sub-dose of compound for a human recipient is about 50 mg.

While it is possible for the active compound previously described to be administered alone as the raw chemical, it is preferable to present the active compound, a compound of formula (I), as a pharmaceutical formulation. Formulations of the present invention, both for veterinary and for human medical use, comprises the active compound together with one or more pharmaceutically acceptable carriers thereof and optionally any other therapeutic ingredients. For example, the active compound may be formulated with a sympathomimetic agent such as the decongestant pseudoephedrine, an antitussive such as codeine, an analgesic, an antiinflammatory, an antipyretic, or an expectorant. The carrier(s) must be pharmaceutically acceptable in the sense of being compatible with the other ingredients of the formulation and not deleterious to the recipient thereof.

The formulations include those suitable for oral, rectal, topical, nasal, ophthalmic or parenteral (including subcutaneous, intramuscular and intravenous) administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier or both and then, if necessary, shaping the product into the desired formulations.

Formulations of the present invention suitable for oral administration may be presented as discrete units such as capsules, cachets, tablets or lozenges, each containing a predetermined amount of the active compound (defined herein as a compound of formula (I)); as a powder or granules; or a suspension in an aqueous liquid or non-aqueous liquid such as a syrup, an elixir, an emulsion or a draught.

A tablet may be made by compression or molding, optionally with one or more accessory ingredients. Compressed tablets may be prepared by compressing in a suitable machine, with the active compound being in a free-flowing form such as a powder or granules which is optionally mixed with a binder, disintegrant, lubricant, inert diluent, surface active agent or dispersing agent. Molded tablets comprised of a mixture of the powdered active compound with any suitable carrier may be made by molding in a suitable machine.

A syrup may be made by adding the active compound to a concentrated, aqueous solution of a sugar for example sucrose to which may also be added any accessory ingredient(s). Such accessory ingredient(s) may include flavourings, an agent to retard crystallization of the sugar or an agent to increase the solubility of any other ingredient, such as a polyhydric alcohol for example, glycerol or sorbitol, and suitable preservatives.

Formulations for rectal administration may be presented as a suppository with a usual carrier such as cocoa butter, or hydrogenated fats or hydrogenated fatty carboxylic acids.

Formulations suitable for parenteral administration conveniently comprise a sterile aqueous preparation of the active compound which is preferably isotonic with the blood of the recipient.

Nasal spray formulations comprise purified aqueous solutions of the active compound with preservative agents and isotonic agents. Such formulations are adjusted to a pH and isotonic state compatible with the nasal mucous membranes.

Ophthalmic formulations are prepared by a similar method to the nasal spray except the pH and isotonic factors are adjusted to match that of the eye.

Topical formulations comprise the active compound dissolved or suspended in media such as mineral oil, petrolatum, polyhydroxy alcohols or other bases used for topical pharmaceutical formulations. The addition of other accessory ingredients, vide infra, may be desirable.

In addition to the aforementioned ingredients, the formulations of this invention may further include one or more accessory ingredient(s) selected from diluents, buffers, flavouring agents, binders, disintegrants, surface active agents, thickeners, lubricants, preservatives (including antioxidants) and the like.

When used in medicine, the salts of the compound of formula (I) should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts include, but are not limited to, those prepared from the following acids: hydrochloric, hydrobromic, sulphuric, nitric, phosphoric, maleic, salicyclic, toluene-p-sulphonic, tartaric, citric, methane-sulphonic, formic, malonic, succinic, naphthalene-2-sulphonic and benzenesulphonic. Also pharmaceutically acceptable salts can be prepared as alkaline metal or alkaline earth salts, such as sodium, potassium or calcium salts of the carboxylic acid group.

The following Examples are provided by the way of illustration of the present invention and should in no way be construed as a limitation thereof. All temperatures indicated are in degrees Celsius.

EXAMPLE 1

(E)-3-(4-Chloro-α-(4-methyl-1-piperazinyl)-benzyl)cinnamic acid

A solution of 4-bromochlorobenzene (20.0 g, 104 mmol) in 125 mL of dry tetrahydrofuran under nitrogen was cooled to −78° and 70 mL of 1.5M n-butyllithium in hexane was added dropwise over 20 minutes. After stirring another 10 minutes, 12.5 mL (104 mmol) of 3-bromobenzaldehyde was added dropwise and the reaction was stirred for another 10 minutes at −78°. Saturated aqueous ammonium chloride (100 mL) was added and the reaction was warmed to room temperature and extracted with 300 mL of ether. The ethereal layer was extracted with three 75 mL portions of 1M sodium bisulfite, 75 mL of 1M sodium hydroxide, 75 mL of water, and 75 mL of brine. The ether layer was dried over magnesium sulfate and the solvent removed to give 31.2 g of 3-bromo-4'-chlorobenzhydryl alcohol as a pale yellow solid. A portion was recrystallized from hexanes containing 5% ether to give white needles, m.p. 67°–68°. Calc. for $C_{13}H_{10}BrClO$: C, 52.47; H, 3.39; Br, 26.85; Cl, 11.91. Found: C, 52.25; H, 3.25; Br, 26.72; Cl, 12.09.

A solution of the above benzhydryl alcohol (13.0 g, 43 mmol) in 100 mL of methylene chloride and 5 mL of pyridine was stirred at room temperature during dropwise addition of 4.7 mL (64 mmol) of thionyl chloride in 20 mL of methylene chloride. After stirring overnight, the reaction solution was washed with two 60 mL portions of 1M hydrochloric acid and 50 mL of water and dried over magnesium sulfate. Evaporation of the solvent gave 14.0 g of 3-bromo-4'-chlorobenzhydryl chloride as a pale yellow oil. A portion was purified by chromatography on silica gel with hexane to give a colorless oil. Calc. for $C_{13}H_9BrCl_2$: C, 49.41; H, 2.87; Br, 25.28; Cl, 22.44. Found: C, 49.50; H, 2.82; Br, 25.27; Cl, 22.48.

The benzhydryl chloride from above (8.33 g, 26.4 mmol) in 10 mL of N-methylpiperazine was heated to 110° for 12 hours under nitrogen. After cooling to room temperature, the residue was dissolved in 75 mL of methylene chloride and washed with 40 mL of 1M sodium hydroxide and two 50 mL portions of water. After drying over sodium sulfate, the solvent was removed in vacuo to give 10.2 g of 1-(3-bromo-4'-chlorobenzhydryl)-4-methylpiperazine as a dark oil. A portion of the oil was dissolved in ether and converted to the dihydrochloride salt with ethanolic hydrogen chloride. Recrystallization from 2:1 ethanol:methanol gave white powdery crystals, m.p. 229°–231°. Calc. for $C_{18}H_{20}BrClN_2.2HCl$: C, 47.76; H, 4.90; N, 6.19. Found: C, 47.55; H, 4.91; N, 6.13.

The benzhydrylpiperazine from above (1.12 g, 2.96 mmol) was dissolved in 6 mL of acetonitrile and placed in a 25 mL Teflon-lined steel bomb with 0.53 mL (6.0 mmol) of methyl acrylate, 0.51 mL (3.7 mmol) of triethylamine, 17 mg (0.075 mmol) of palladium acetate, and 31 mg (0.12 mmol) of triphenylphosphine. The bomb was sealed and heated at 125° for 24 hours. The contents were dissolved in 20 mL of 1M hydrochloric acid and extracted with two 20 mL portions of ether. The acid layer was basified with 1M sodium hydroxide and extracted with 40 mL and 10 mL portions of chloroform. The combined chloroform extracts were dried over sodium sulfate and the solvent was removed to give 1.00 g of residue. Chromatography on silica gel (Waters Prep 500, methylene chloride containing 0.5% ethanol and 0.1% triethylamine) gave 433 mg (38%) of methyl (E)-3-(4-chloro-α-(4-methyl-1-piperazinyl)benzyl)cinnamate as a colorless oil.

The ester from above (1.05 g, 2.73 mmol) was dissolved in 20 mL of methanol with 8 mL of 1M potassium hydroxide and stirred overnight at room temperature. The methanol was removed in vacuo and the remaining aqueous solution was extracted with two 15 mL portions of ether. The aqueous layer was adjusted to a pH of 7 with 1M hydrochloric acid. The solution was chilled and the white powdery precipitate was collected by filtration to give 504 mg (46%) of (E)-3-(4-chloro-α-(4-methyl-1-piperazinyl)benzyl)cinnamic acid, m.p. 131°–141°. Calc. for $C_{21}H_{23}ClN_2O_2.2H_2O$: C, 61.99; H, 6.69; N, 6.88; Cl, 8.71. Found: C, 61.98; H, 6.72; N, 6.89; Cl, 8.66.

EXAMPLE 2

3-(4-Chloro-α-(4-methyl-1-piperazinyl)benzyl)benzoic acid

The intermediate from Example 1, 1-(3-bromo-4'-chlorobenzhydryl)-4-methylpiperazine (1.10 g, 2.90 mmol), was dissolved in 10 mL of dry tetrahydrofuran and dried further over 4A molecular sieves for 24 hours. The solution was transferred to a dry flask under nitrogen and cooled to −78°. n-Butyllithium in hexane (1.1M, 2.6 ml) was added dropwise and the solution was stirred for 10 minutes at −78°. Carbon dioxide gas was bubbled into the reaction until the red solution turned yellow. The reaction was warmed to room temperature and the solvent was evaporated. The residue was dissolved in 20 mL of water and made basic with several drops of 1M sodium hydroxide. The aqueous solution was extracted with two 50 mL portion of ether and the pH was adjusted to 7–8 with 1M hydrochloric acid. After chilling in an ice bath, the precipitate was collected by filtration to give 341 mg (33%) of 3-(4-chloro-α-(4-methyl-1-piperazinyl)benzyl)benzoic acid as a white powder, m.p. 225°–230° (dec.). Calc. for $C_{19}H_{21}ClN_2O_2.0.75 H_2O$: C, 63.68; H, 6.33; N, 7.82; Cl, 9.89. Found: C, 63.68; H, 6.34; N, 7.82; Cl, 9.89.

The following Examples 3–5 were prepared by procedures similar to those used in obtaining Example 2.

EXAMPLE 3

2-(4-Chloro-α-(4-methyl-1-piperazinyl)benzyl)benzoic acid

Starting initially with 4-bromochlorobenzene and 2-bromobenzaldehyde, the final product was obtained as an off-white powder, m.p. 144°–150°. Calc. for $C_{19}H_{21}ClN_2O_2.H_2O$: C, 62.89; H, 6.39; N, 7.72; Cl, 9.77. Found: C, 63.07; H, 6.03; N, 7.79; Cl, 9.77.

EXAMPLE 4

4-(4-Chloro-α-(4-methyl-1-piperazinyl)benzyl)benzoic acid

Starting initially with 4-bromochlorobenzene and 4-bromobenzaldehyde, the final product was obtained as an off-white powder, m.p. 250°–255° (dec.). Calc. for $C_{19}H_{21}ClN_2.0.25 H_2O$: C, 65.32; H, 6.20; N, 8.02; Cl, 10.15. Found: C, 65.23; H, 6.24; N, 8.02; Cl, 10.14.

EXAMPLE 5

3-(4-Methoxy-α-(4-methyl-1-piperazinyl)benzyl)benzoic acid

Starting initially with 4-bromoanisole and 3-bromobenzaldehyde, the final product was obtained as an impure solid which was converted to its oxalate salt and purified by crystallization from ethanol and ether to give a pale yellow powder, m.p. 120°–130° (dec.). Calc. for $C_{20}H_{24}N_2O_3.C_2H_2O_4.H_2O.0.5 C_2H_5OH$: C, 58.59; H, 6.63; N, 5.94. Found: C, 58.23; H, 6.24; N, 5.86.

EXAMPLE 6

3-(4-Chloro-α-(4-methyl-1-piperazinyl)benzyl)phenoxyacetic acid

By the same method used in Example 1 for preparing 1-(3-bromo-4'-chlorobenzyhydryl)-4-methylpiperazine, the preparation of 1-(3-benzyloxy-4'-chlorobenzhydryl)-4-methylpiperazine was accomplished starting with 4-bromochlorobenzene and 3-benzyloxybenzaldehyde. The final product was obtained as a white dihydrochloride salt, m.p. 168°–172°. Calc. for $C_{25}H_{27}ClN_2O.2HCl.0.75\ H_2O$: C, 60.86; H, 6.23; N, 5.68; Cl, 21.56. Found: C, 60.63; H, 5.94; N, 5.64; Cl, 21.40.

The dihydrochloride salt from above (12.0 g, 25 mmol) was suspended in 250 mL of methylene chloride and 50 mL of 0.5M boron tribromide in methylene chloride was added dropwise at room temperature. The reaction was stirred overnight and quenched by addition of 200 mL of methanol. The solvent was removed in vacuo and the residue was dissolved in 500 mL of water. After extraction with two 150 mL portions of ether, the aqueous layer was adjusted to a pH of 9 with 1M sodium hydroxide and extracted with four 200 mL portions of ether. The latter ether extract was dried over sodium sulfate and the solvent was removed to give 8.50 g of the resulting phenol, which was used without further purification.

A portion of the phenol (4.27 g, 13.5 mmol) was dissolved in 50 mL of dry tetrahydrofuran and added slowly to 650 mg (13.5 mmol) of 50% sodium hydride dispersion under nitrogen. The reaction was heated to reflux briefly to complete anion formation. After cooling to room temperature, 1.49 mL (13.5 mmol) of ethyl bromoacetate was added and the reaction was stirred for one hour. The reaction was diluted with 150 mL of ether and extracted with 90 mL of 0.3M hydrochloric acid. The aqueous layer was made basic with 1M sodium hydroxide and extracted with two 75 mL portions of ether. The extracts were dried over sodium sulfate and the solvent removed to give 3.98 g of ethyl 3-(4-chloro-α-(4-methyl-1-piperazinyl)benzyl)phenoxyacetate as a yellow oil.

The ester from above (4.45 g, 11.0 mmol) was dissolved in 60 mL of methanol with 22 mL of 1M potassium hydroxide and stirred overnight at room temperature. The methanol was removed in vacuo and the remaining aqueous solution was diluted to 40 mL with water and extracted with 50 mL of ether. The aqueous solution was concentrated to 20 mL and 1M hydrochloric acid was added dropwise until precipitation occurred at a pH of 5. After settling for several hours, the supernatant was decanted from the oily yellow precipitate which was presumably the hydrochloride salt. Repeated attempts to crystallize this material were unsuccessful. The remaining product (1.8 g) was dissolved in 20 mL of 1M potassium hydroxide and the pH adjusted to 5 with 0.5M oxalic acid. The supernatant was decanted from the oily yellow precipitate, which was dissolved in 2:1 ethanol:methanol with excess oxalic acid and heat. Granular white crystals of the dioxalate salt formed upon cooling. A portion was recrystallized twice from 2:1 ethanol:methanol to give white prisms of 3-(4-chloro-α-(4-methyl-1-piperazinyl)benzyl)phenoxyacetic acid dioxalate, m.p. 173°–175° (dec.). Calc. for $C_{20}H_{23}ClN_2O_3.2\ C_2H_2O_4$: C, 48.42; H, 4.53; N, 4.34; Cl, 5.50. Found: C, 48.21; H, 4.57; N, 4.48; Cl, 5.73.

EXAMPLE 7

3-(4-Chloro-α-(4-(3-methylbenzyl)-1-piperazinyl)benzyl)phenoxyacetic acid

The ester ethyl 3-(4-chloro-α-(4-(3-methylbenzyl)-1-piperzinyl)benzyl)phenoxyacetate was prepared in a fashion analogous to the procedure of Example 6. The ester (4.8 g, 10 mmol) was dissolved in 90 mL of methanol with 10 mL of 4M potassium hydroxide. After stirring overnight at room temperature, the reaction solution was decanted from a small amount of gummy precipitate and evaporated to dryness. The residue was dissolved in chloroform and shaken with 50 mL of 1M hydrochloric acid, extracting the acid layer with a second portion of chloroform. The chloroform extracts were dried over magnesium sulfate and the solvent removed to give 5.1 g of beige foam. The product was crystallized from benzene containing a trace of ethanol to give 2.06 g of 3-(4-chloro-α-(4-(3-methylbenzyl)-1-piperazinyl)benzyl)phenoxyacetic acid as a hygroscopic white powder, m.p. 114°–120°. Calc. for $C_{27}H_{29}ClN_2O_3.0.3\ C_6H_6.0.6\ H_2O$: C, 69.29; H, 6.46; N, 5.61; Cl, 7.10. Found: C, 69.30; H, 6.30; N, 5.43; Cl, 7.09.

EXAMPLE 8

3-(4-Chloro-α-(4-(4-tert-butylbenzyl)-1-piperazinyl)benzyl)phenoxyacetic acid The title compound was prepared in the same way as Example 7 and was isolated as its hydrochloride salt by evaporating a solution in 5% isopropanol:benzene to give a hygroscopic white powder, m.p. 115°–125° (dec.). Calc. for $C_{30}H_{35}ClN_2O_3.HCl.0.5\ C_6H_6.0.75\ H_2O$: C, 66.49; H, 6.85; N, 4.70; Cl, 11.89. Found: C, 66.14; H, 6.47; N, 4.71; Cl, 11.62.

EXAMPLE 9

Antihistaminic Activity

In vitro antihistaminic activity: The longitudinal muscle was isolated from the intact ileum of guinea-pigs (Hartley, male, 250–400 g) and placed in an organ bath under 300 mg tension. After one hour of equilibration, cumulative concentration-response curves (Van Rossum, J. M., *Arch. Int. Pharmacodyn. Ther.* 143, 299–330, 1963) to histamine were obtained. Following washing, the tissues were incubated for one hour with the test compound and then a second histamine concentration-response curve was run. Antihistaminic activity was determined as $pA_2$ values by the method of Arunlakshana, O. and Schild, H. O. (*Br. J. Pharmacol.* 14, 48–58, 1959).

TABLE I

| Results of Antihistamine Assays | |
|---|---|
| Compound | $pA_2$* |
| Chlorcyclizine | 8.6** |
| A | 6.3 |
| B | 6.4 |
| C | 5.6 |
| D | 5.6 |
| E | 6.5 |
| F | 6.8 |
| G | 8.8 |
| H | 8.2 |

*Denotes the negative log of the concentration which gives a significant antihistaminic effect (higher $pA_2$ values indicate more potent antihistaminic activity).
**R. B. Barlow, Introduction to Chemical Pharmacology, 2nd ed., p. 357, Wiley, New York, 1964.

EXAMPLE 10

Formulations

| (A)-Injection | |
|---|---|
| Ingredient | Amount per ampoule |
| Compound of formula (I) | 50.0 mg |
| Water for Injections, q.s. | 1.0 mL |

The finely ground active compound was dissolved in the water for Injections. The solution was filtered and sterilized by autoclaving.

| (B)-Suppository | |
|---|---|
| Ingredient | Amount per suppository |
| Compound of Formula (I) | 50.0 mg |
| Cocoa Butter, or Wecobee TM Base q.s. | 2.0 g |

Wecobee is a trademark and is a hydrogenated fatty carboxylic acid.

The finely ground active compound was mixed with the melted suppository base (either Cocoa Butter or Wecobee TM base), poured into molds and allowed to cool to afford the desired suppositories.

| (C)-Syrup | |
|---|---|
| Ingredient | Amount per 5 mL |
| Compound of Formula (I) | 50.0 mg |
| Ethanol | 0.3 mg |
| Sucrose | 2.0 mg |
| Methylparaben | 0.5 mg |
| Sodium Benzoate | 0.5 mg |
| Cherry Flavour | q.s. |
| Coloring | q.s. |
| Water | q.s. to 5.0 mL |

Ethanol, sucrose, sodium benzoate, methylparaben, and flavouring were combined in 70% of the total batch quantity of water. Coloring and the active compound were dissolved in the remaining water, then the two solutions were mixed and clarified by filtration.

| (D)-Tablet | |
|---|---|
| Ingredient | Amount per Tablet |
| Compound of Formula (I) | 50.0 mg |
| Lactose | 110.0 mg |
| Corn Starch, Pregelatinized | 2.5 mg |
| Potato Starch | 12.0 mg |
| Magnesium stearate | 0.5 mg |

The active compound was finely ground and intimately mixed with the powdered excipients lactose, corn starch, potato starch, and magnesium stearate. The formulation was then compressed to afford a tablet weighing 175 mg.

| (E)-Capsule | |
|---|---|
| Ingredient | Amount per Capsule |
| Compound of Formula (I) | 50.0 mg |
| Lactose | 440.0 mg |
| Magnesium Stearate | 5.0 |

The finely ground active compound was mixed with the powdered excipients lactose, corn starch, and stearic acid and packed into gelatin capsules.

| (F)-Tablet | |
|---|---|
| Ingredient | Amount per Tablet |
| Compound of Formula (I) | 50.0 mg |
| Pseudoephedrine HCl | 60.0 mg |
| Lactose | 62.5 mg |
| Potato Starch | 14.0 mg |
| Magnesium Stearate | 1.0 mg |
| Gelatin | 2.8 mg |

A tablet was prepared from the above formulation by the method previously described in Example 7 (D).

| (G)-Syrup | |
|---|---|
| Ingredient | Amount per 5 mL |
| Compound of Formula (I) | 50.0 mg |
| Pseudoephedrine HCl | 30.0 mg |
| Codeine Phosphate | 10.0 mg |
| Guaifenesin | 100 mg |
| Methylparaben | 0.5 mg |
| Sodium benzoate | 0.5 mg |
| Flavor | q.s. |
| Color | q.s. |
| Glycerol | 500 mg |
| Sucrose | 2000 mg |
| Purified Water | q.s. to 5.0 mL |

A syrup containing other active ingredients in addition to a compound of formula (I) was prepared from the above ingredients by an analogous method to that described for Example 7 (C) above.

| (H)-Nasal Spray | |
|---|---|
| Ingredient | Amount per 100.0 mL |
| Compound of Formula (I) | 5 g |
| Sodium Chloride | 0.8 g |
| Preservative | 0.5 g |
| Purified Water | q.s. 100.0 mL |

The preservative was dissolved in warm purified water and after cooling to 25°–30° C. the sodium chloride and the compound of formula (I) were added. The pH was then adjusted to 5.5–6.5 and purified water was added to bring the final volume to 100.0 mL.

| (I)-Ophthalmic Solution | |
|---|---|
| Ingredient | Amount per 100.0 mL |
| Compound of Formula (I) | 1.0 g |
| Sodium Chloride | 0.8 g |
| Preservative | 0.5 g |
| Water for Injection | q.s. 100.0 mL |

This formulation was prepared in a similar way to the nasal spray.

| (J)-Topical Cream | |
|---|---|
| Ingredient | Amount per 100 g |
| Compound of Formula (I) | 5.0 g |
| Emulsifying Wax, N.F. | 15.0 g |
| Mineral Oil | 5.0 g |
| White Petrolatum | 5.0 g |
| Preservative | 0.25 g |
| Purified Water | q.s. 100 g |

The preservative was dissolved in approximately 50 g of warm purified water and after cooling to about 25°–30° the compound of formula (I) was added. In a separate container the emulsifying wax, mineral oil, and white petrolatum were mixed well and heated to approximately 70°–80° C. The aqueous solution containing the compound of formula (I) was added to the warm mixture of emulsifying wax, mineral oil, and petrolatum with vigorous mixing while cooling to 25° C. Additional purified water was added with mixing to bring the total amount to 100.0 g.

| (K)-Topical Lotion | |
| --- | --- |
| Ingredient | Amount per 100 mL |
| Compound of Formula (I) | 50.0 g |
| Carbomer, N.F. | 0.15 g |
| Triethanolamine | 0.15 g |
| Preservative | 0.5 g |
| Propyleneglycol | 5.0 g |
| Purified Water | q.s. 100 mL |

The preservative was dissolved in approximately 50 g of warm purified water and after this solution was cooled to 25°–30° C., the compound of formula (I) was added. The carbomer was mixed in next followed by triethanolamine and propyleneglycol. Purified water was added to bring the total amount to 100 mL and the formulation was mixed well.

We claim:

1. A compound selected from the group comprising:

(E)-3-(4-chloro-α-(4-methyl-1-piperazinyl)benzyl)-cinnamic acid;

3-(4-chloro-α-(4-methyl-1-piperazinyl)benzyl)benzoic acid;

2-(4-chloro-α-(4-methyl-1-piperazinyl)benzyl)benzoic acid;

4-(4-chloro-α-(4-methyl-1-piperazinyl)benzyl)benzoic acid;

3-(4-methoxy-α-(4-methyl-1-piperazinyl)benzyl)benzoic acid;

3-(4-chloro-α-(4-methyl-1-piperazinyl)benzyl)phenoxyacetic acid;

3-(4-chloro-α-(4-(3-methylbenzyl)-1-piperazinyl)benzyl)phenoxyacetic acid;

3-(4-chloro-α-(4-(4-tert-butylbenzyl-1-piperazinyl)benzyl phenoxyacetic acid;

and pharmaceutically acceptable acid addition salt, esters and amides thereof.

2. A method of treating a human having elevated histamine levels which comprises administering to said human an effective antihistamine amount of the compound, pharmaceutically acceptable salt, ester or amide of claim 1 to said human.

3. A method of treating a human having elevated histamine levels which comprises administering to said human an effective antihistamine amount of the compound or a pharmaceutically acceptable acid addition salt of claim 1 to said human.

* * * * *